United States Patent
Unger et al.

(10) Patent No.: US 9,314,653 B2
(45) Date of Patent: Apr. 19, 2016

(54) SORBING GRANULAR MATERIAL AND PROCESS FOR PRODUCING SORBING GRANULAR MATERIAL

(75) Inventors: Jürgen Unger, Berlin (DE); Annette Kosegarten, Krummesse (DE)

(73) Assignee: Dräger Safety AG & Co. KGaA, Lübeck (DE)

(*) Notice: Subject to any disclaimer, the term of this patent is extended or adjusted under 35 U.S.C. 154(b) by 839 days.

(21) Appl. No.: 13/242,313

(22) Filed: Sep. 23, 2011

(65) Prior Publication Data
US 2012/0247461 A1 Oct. 4, 2012

(30) Foreign Application Priority Data
Mar. 31, 2011 (DE) .......................... 10 2011 015 723

(51) Int. Cl.
| | |
|---|---|
| A61M 16/22 | (2006.01) |
| A61M 16/10 | (2006.01) |
| B01J 20/04 | (2006.01) |
| B01J 20/20 | (2006.01) |
| A62B 23/02 | (2006.01) |
| B01D 39/06 | (2006.01) |
| B01J 20/30 | (2006.01) |

(Continued)

(52) U.S. Cl.
CPC ................ *A62B 23/02* (2013.01); *A61M 16/22* (2013.01); *B01D 39/06* (2013.01); *B01J 20/041* (2013.01); *B01J 20/28009* (2013.01); *B01J 20/3028* (2013.01); *B01J 20/3035* (2013.01); *A61M 16/01* (2013.01); *A61M 16/104* (2013.01)

(58) Field of Classification Search
CPC . A61M 16/22; A61M 16/104; A61M 16/105; A61M 16/01; B03C 1/32; B01D 2247/02; B01D 39/06; B01D 39/2058; B01D 39/2055; B01J 20/28009

USPC ............. 128/205.27, 205.28, 205.29, 206.17; 55/DIG. 33, DIG. 35; 95/27, 28; 96/1
See application file for complete search history.

(56) References Cited

U.S. PATENT DOCUMENTS

| | | | |
|---|---|---|---|
| 5,038,767 A | 8/1991 | Jumpertz | |
| 5,487,380 A * | 1/1996 | Grabenkort | .............. 128/204.15 |

(Continued)

FOREIGN PATENT DOCUMENTS

| | | |
|---|---|---|
| DE | 39 01 062 A1 | 7/1990 |
| DE | 39 17 096 C1 | 8/1990 |

(Continued)

OTHER PUBLICATIONS

"Carpenter Technologies, Magnetic Properties of Stainless Steels," http://www.cartech.com/techarticles.aspx?id=1476, dated Jun. 2006, retrieved Jun. 23, 2014.*

*Primary Examiner* — Justine Yu
*Assistant Examiner* — Douglas Sul
(74) *Attorney, Agent, or Firm* — McGlew and Tuttle, P.C.

(57) ABSTRACT

A sorbing granular material (20) is provided including a plurality of particles of granular material (5). The particles of granular material (5) are mixed at least partly with magnetizable particles (10), so that in case of magnetization of the magnetizable particles (10), the particles of granular material (5) form a compacted sorbing granular material (20) based on magnetic attracting forces between the magnetizable particles (10). The compaction is reversible. In addition, a process for producing a sorbing granular material (20) is provided.

20 Claims, 3 Drawing Sheets

(51) Int. Cl.
*B01J 20/28* (2006.01)
*A61M 16/01* (2006.01)

(56) References Cited

U.S. PATENT DOCUMENTS

| | | | | |
|---|---|---|---|---|
| 6,706,097 | B2* | 3/2004 | Zornes | 96/153 |
| 8,283,185 | B2* | 10/2012 | Paul et al. | 436/526 |
| 8,454,726 | B2* | 6/2013 | Haugan | 95/27 |
| 2006/0133975 | A1* | 6/2006 | Yamanaka et al. | 423/210 |
| 2007/0160512 | A1* | 7/2007 | Ohmi et al. | 422/186.03 |
| 2008/0283059 | A1* | 11/2008 | Siegel et al. | 128/203.25 |
| 2008/0307960 | A1* | 12/2008 | Hendrickson et al. | 95/28 |

FOREIGN PATENT DOCUMENTS

| | | |
|---|---|---|
| DE | 197 40 736 A1 | 3/1999 |
| DE | 100 65 761 A1 | 7/2002 |
| DE | 101 60 664 A1 | 6/2003 |
| DE | 102 10 786 A1 | 10/2003 |
| DE | 100 47 137 B4 | 9/2005 |
| EP | 0 130 043 B1 | 12/1987 |
| EP | 02 94 707 A2 | 12/1988 |
| EP | 0 142 903 B1 | 9/1989 |
| EP | 0 339 487 A2 | 11/1989 |
| EP | 0 387 394 B1 | 12/1993 |
| WO | 9817375 A1 | 4/1998 |

* cited by examiner

SORBING GRANULAR MATERIAL AND PROCESS FOR PRODUCING SORBING GRANULAR MATERIAL

CROSS REFERENCE TO RELATED APPLICATIONS

This application claims the benefit of priority under 35 U.S.C. §119 of German Patent Application 10 2011 015 723.9 filed Mar. 31, 2011, the entire contents of which are incorporated herein by reference.

FIELD OF THE INVENTION

The present invention pertains to a sorbing granular material and to a process for producing a sorbing granular material, especially as granular absorbents or adsorbents for cleaning gas in personal protective gear or for use in anesthesia apparatuses.

BACKGROUND OF THE INVENTION

Personal protective gear has come into use in many areas in order to protect the user from hazards. For example, members of firefighting crews and technical relief organizations are equipped with protective gear in order to be able to be deployed during their missions without hazards or with reduced hazard. Personal protective gear is also used in the area of workplace protection, for example, when handling chemicals. Further applications pertain, for example, to devices known as closed-circuit devices, in which the carbon dioxide expired by the user is removed from the breathing air.

Other fields of application of protective gear pertain to medical staff, which shall be protected from infectious diseases while in contact with patients.

The removal or abatement of gaseous harmful substances from gas flows is described, in general, as a mass transfer process and is of prominent significance especially in the area of personal respirators. In conjunction with breathing masks, escape hoods, closed-circuit or regeneration type respirators, filters and/or filter inserts protect the human user from vapors and gases that are hazardous to health.

The harmful substances are either retained in this case in corresponding absorbents or adsorbents or converted by chemical reactions into harmless substances.

One example of the chemical conversion of undesired or harmful substances into harmless substances is the processing of breathing gas in closed-circuit or regeneration type respirators by the use of so-called breathing lime, which binds the expired carbon dioxide.

Breathing lime is also used, besides in the said respirators, in the area of medicine in anesthesia apparatuses and respirators. Anesthesia apparatuses shall be mentioned, in particular, in this connection, in which the breathing air mixed with an inhalation anesthetic is inspired and then expired by the patient in a closed circuit, while the carbon dioxide present is bound or removed by the use of breathing lime.

Harmful expired $CO_2$ is chemically bound on the absorbent in these applications, e.g., in a chemical reaction, as it appears clearly from the following reaction equations. Water as well as heat are generated as a result with a reaction enthalpy of $\Delta HR = -113$ kJ/mol $CO_2 + H_2O \rightarrow H_2CO_3$ $H_2CO_3 + 2NaOH \rightarrow Na_2CO_3 + 2H_2O$ $Na_2CO_3 + Ca(OH)_2 \rightarrow CaCO_3 + 2NaOH$ $Ca(OH)_2 + CO_2 \rightarrow CaCO_3 + H_2O$ One example for the retention of undesired or harmful substances by corresponding adsorbents is the use of activated carbon as a respirator filter material.

As is known in industry, activated carbon consists of carbon with a highly porous structure. The inner surface is said to be 300 to 2,000 $m^2$ per g of carbon. The harmful gases become attached to the inner pores of the activated carbon, and the adsorption properties depend on the pore size distribution.

Absorbents and/or adsorbents for cleaning gases, which are used in the area of personal respirators, are produced in various granular forms. The granular material guarantees a sufficiently large reaction surface for the gas cleaning with at the same time a sufficiently low flow resistance of a filter cartridge filled with absorbent/adsorbent.

The formation of ducts within the granular material filling or at the edges towards the cartridge must be prevented from occurring by all means in the filled cartridges or filter cartridges when granular materials are used. Such ducts may very greatly reduce the performance of such a filter and thus potentially jeopardize the user.

The cause of such duct formation may be an unintended relative motion of the particles of the granular material among each other.

Another undesired effect of the relative motion is the abrasion of the absorbent/adsorbent, which occurs in the process. The abrasion dust must possibly be removed in a complicated manner after longer shipping before the use of the absorbent/adsorbent.

The user's health may possibly be jeopardized if larger quantities of dust enter the user's airways.

To fill the filter cartridges/absorber containers, the absorbent granular materials and/or adsorbent granular materials are filled typically through sieves, which affect the motion of the falling particles of granular material such that a maximum bulk density is obtained depending on the particle size. The inlet and outlet openings are then closed by relatively rigid sieves or sieve plates. The compression forces applied by the sieves on the granular material filling limit the relative motion of the particles of granular material.

A corresponding device is described in the document DE 39 17 096 C1. A container for a chlorate candle is shown in this document, which is filled with a granular chemical and has a bottom plate, which is pressed against the chemical by means of a spring.

However, the drawback of such a solution is that the compression forces cannot be applied uniformly to the filling and can be completely abolished by friction between the particles.

Another drawback is that the inlet and outlet are closed with sieves, which leads to an impairment of the flow through the absorber filling.

The packing density of the bulk material may be reduced by storage, which is often associated with a shrinkage of the particles, as well as by shipping.

Other solutions are based on filter bodies made of multi-layer fabric and/or knitted fabrics, which is manufactured from fibrous material and/or wire or open-cell plastic foam or nonwoven. The particles of granular material are then bound in these filter bodies, for example, with adhesives or adhesive liquids.

European Patent EP 0 387 394 B1 describes a process for producing a filter body with the use of an adhesive liquid.

European Patent EP 0 339 487 A2 discloses an activated carbon layer for gas masks as an air-permeable flat object with a granular layer or a layer consisting of beads consisting of activated carbon, which are bound to the flat object with hot melt adhesive.

European Patent Application EP 0 294 707 discloses a breathing mask made of filtering material in the form of an open-cell foam material, which contains the adsorber particles.

Patent Application WO 98/17375 discloses an absorber/adsorber body, which consists of a wound, furrowed adsorber mat, in which flow ducts are formed by the furrowing.

One drawback of these solutions is, on the one hand, the reduced efficiency of such filter bodies as well as the increased flow resistance. Another drawback is the complicated manufacture of such solutions. The lateral sealing against the wall of a filter cartridge likewise requires increased effort. In case of the absorber roll, mechanical damage to the roll, which cannot be ruled out, may possibly lead to so-called bypass flows and undesired breakthroughs of harmful substances.

SUMMARY OF THE INVENTION

A basic object of the present invention is therefore to overcome the above-described drawbacks of the state of the art by reducing the undesired relative motion among the particles of granular material.

This object is accomplished according to the present invention in a first aspect by a sorbing granular material comprising a plurality of particles of granular material, where the particles of granular material are mixed at least partly with magnetizable particles, so that in case of magnetization of the magnetizable particles, the granular material particles form a compacted sorbing granular material by means of magnetic attracting forces between the magnetizable particles, wherein the compaction is reversible.

Granular absorbents/adsorbents are compacted according to the present invention such that both a relative motion among the particles of granular material and a motion between the granular material and a surrounding wall of, for example, a filter cartridge or a breathing lime absorber is prevented or greatly reduced.

The magnetizable particles are mixed with sorbing raw material in one embodiment.

In another embodiment, the magnetizable particles are arranged on outer surfaces of sorbing raw material or on outer surfaces of the granular material bodies.

The sorbing granular material may possess absorbing and/or adsorbing properties.

The magnetizable particles may be added to the sorbing raw material or the granular material body as soft magnetic particles and/or hard magnetic particles.

In one embodiment, the soft magnetic particles are produced as metal particles with a relative permeability between 300 and 10,000, as amorphous metal particles with a relative permeability between 700 and 500,000, or as nanocrystalline metal particles with a relative permeability between 20,000 and 150,000.

The soft magnetic particles may be produced from iron oxide, iron powder and/or steel.

In one embodiment, the hard magnetic particles are produced from hard ferrite, aluminum-nickel-cobalt, neodymium-iron-boron and/or samarium-cobalt.

The magnetization of the magnetizable particles may be carried out by means of an electromagnet or by means of a permanent magnet.

In a second aspect, the above-mentioned object is also achieved according to the present invention by a process for producing a sorbing granular material, wherein the following steps are carried out:

Providing a sorbing raw material;

mixing of a plurality of particles of granular material consisting of the sorbing raw material, wherein in case of magnetization of the magnetizable particles, the particles of granular material form a compacted sorbing granular material by means of magnetic attracting forces.

The formation of a plurality of particles of granular material may also comprise drying and pressing of the sorbing raw material, the particles of granular material being produced by shaping or punching.

In addition, a filter insert for a respirator is provided, wherein said filter insert has a container for filling with a sorbing granular material.

Furthermore, a process for the use of a sorbing granular material in a filter insert or in a shipping or storage vessel is provided, wherein said sorbing granular material is compacted by the filling being exposed to a magnetic field.

The intensity of the necessary magnetic field and/or necessary size, number and material of the magnetizable particles are selected in this process depending on the size and shape of the particles of granular material as well as depending on the occurring or expected external effects, such as shock, vibration or temperature.

The use of the sorbing granular material is suitable for both cylindrical and cuboid filter cartridge geometries or geometries of breathing lime and/or shipping containers.

In addition, an anesthesia apparatus is provided, which comprises an absorbing granular material, which is suitable for absorbing expired breathing air and which has particles of granular material, which are mixed at least partly with magnetizable particles, so that in case of magnetization of the magnetizable particles, the particles of granular material form a compacted sorbing granular material by means of magnetic attracting forces between the magnetizable particles, and the compaction is reversible.

In one embodiment of the present invention, breathing lime is provided for an anesthesia apparatus, for a closed-circuit respirator or for a regeneration type respirator, which comprises an absorbing granular material, which is suitable for absorbing breathing air and which has particles of granular material, which are mixed at least partly with magnetizable particles, so that in case of magnetization of the magnetizable particles, the particles of granular material form a compacted sorbing granular material by means of magnetic attracting forces between the magnetizable particles, and said compaction is reversible.

Furthermore, a filter for an anesthesia apparatus is provided, which comprises an absorbing granular material, which is suitable for absorbing expired breathing air and has a plurality of particles of granular material, which are mixed at least partly with magnetizable particles, so that in case of magnetization of the magnetizable particles, the particles of granular material form a compacted sorbing granular material by means of magnetic attracting forces between the magnetizable particles, wherein said compaction is reversible.

The present invention will be explained in more detail below on the basis of exemplary embodiments with reference to the attached drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1A:
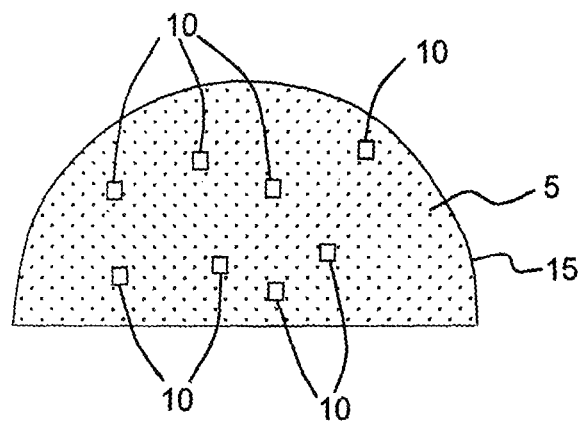
FIG. 1A is a top view showing an arrangement according to the present invention with a particle of granular material according to a first exemplary embodiment.
Figure 1B:
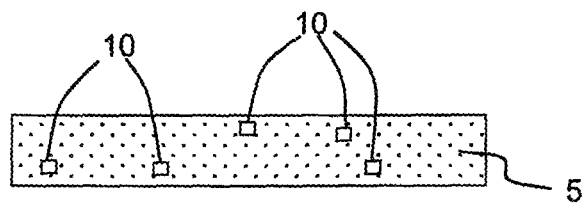
FIG. 1B is a cross-sectional view showing the arrangement according to the present invention with the particle of granular material according to FIG. 1A.

Referring to the drawings in particular, with reference to FIG. 1A and FIG. 1B, a first embodiment of the present invention will be explained below. FIG. 1A shows a particle of granular material 5 in a top view and FIG. 1B shows a corresponding cross-sectional view.

The particle of granular material 5 shown is produced from a sorbing raw mass, which may be designed both as an adsorbing raw mass and as an absorbing raw mass or as an absorbent or adsorbent. The absorbent/adsorbent is mixed with magnetizable particles 10 during its production or before its granulation. In the exemplary embodiment being shown, the magnetizable particles may be mixed with the adsorber/absorber raw mass prior to granulation, so that the magnetizable particles 10 are distributed over the entire particle of granular material 5.

Figure 2A:
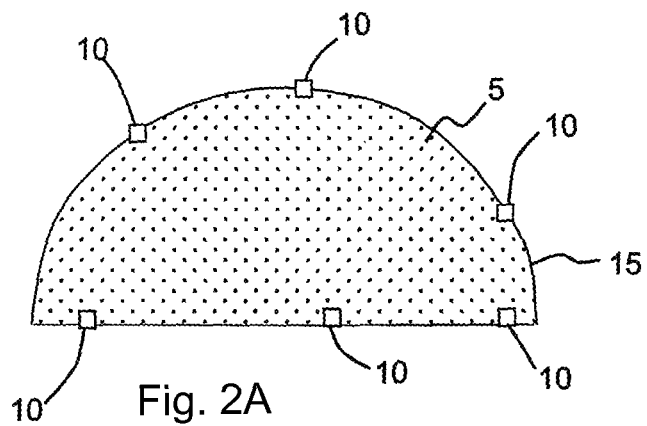
FIG. 2A is a top view showing an arrangement according to the present invention of particle of granular material according to a second exemplary embodiment.
Figure 2B:
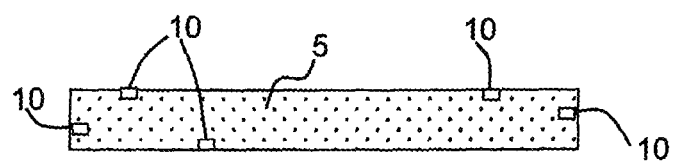
FIG. 2B is a cross-sectional view showing the arrangement according to the present invention of the particle of granular material according to FIG. 2A.

A second embodiment of the present invention is shown in FIG. 2A and FIG. 2B. This embodiment differs from the first one in that the magnetizable particles are placed only on the outer surfaces 15 of the particle of granular material 5.

A sorbing granular material, which is as a result an absorbent/adsorbent granular material possessing another, advantageously utilizable property, is obtained by joining many of these particles of granular material 5.

An advantageous use consists of the gentle compaction of the granular material, as will be shown below with reference to FIG. 3.

Figure 3:
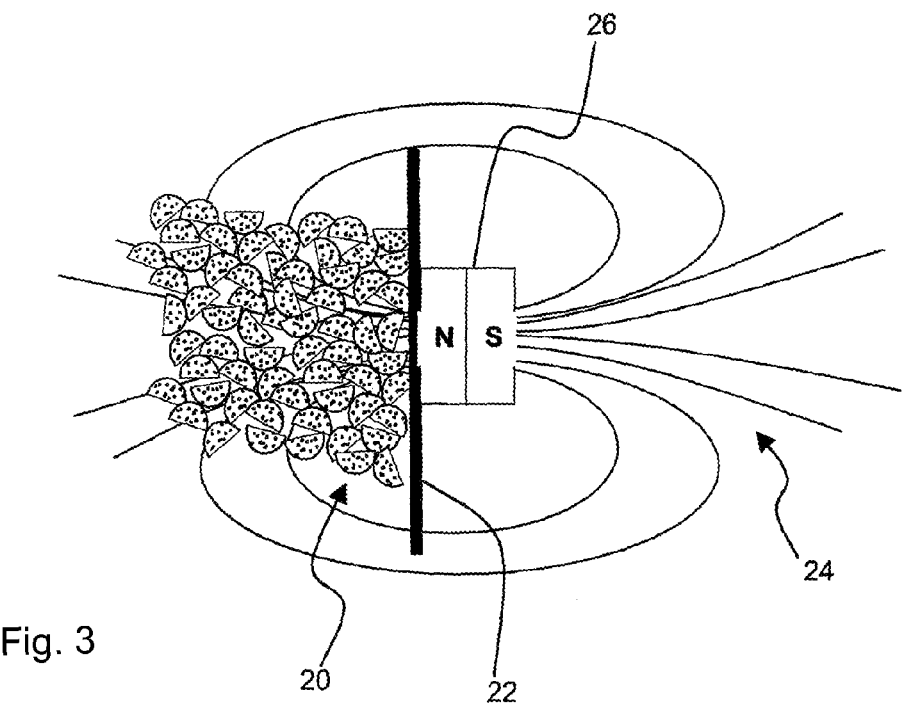
FIG. 3 is a side view showing an arrangement according to the present invention of a granular material comprising a plurality of particles of granular material.

FIG. 3 shows the sorbing granular material 20, which is built up of a plurality of the sorbing particles of granular material 5. The granular material 20 is designed as a filling, for example, in a filter cartridge or an absorption, shipping or storage vessel, as is schematically indicated by the boundary 22 in FIG. 3. The filling is exposed to a magnetic field 24, which is generated by a magnet.

The magnetic field 24 may be generated electromagnetically or also applied by one or more permanent magnets 26. The sorbing particles of granular material 5, which are now magnetic, thus form a stable granular material composite, which no longer permits a relative motion of the particles of granular material 5 among each other. This process can be made reversible by removing or abolishing the magnetic field 24.

All soft or hard magnetic materials, e.g., iron oxide and/or iron powder or particles consisting of steel as soft magnetic materials may be used as materials for the magnetizable particles 10. Hard magnetic materials are, among other things, hard ferrite HF, aluminum-nickel-cobalt AlNiCo, neodymium-iron-boron NdFeB, and samarium-cobalt Sm/Co.

The advantage of soft magnetic materials is that they reach their magnetic saturation already at low field intensities. However, they lose their magnetic action outside the magnetic field 24. To compact the granular material 20, a permanent external magnetic field 24 is therefore necessary when soft magnetic additives are used for the absorbent/adsorbent.

If hard magnetic materials are exposed to a sufficiently strong magnetic field 24, these will have a magnetic field of their own after removal of the external magnetic field 24. If hard magnetic additives are added to the absorber granular material or the adsorber granular material, an external magnetic field 24 must be applied to compact the granular material 20 until the magnetic saturation of the magnetic particles 10 added is reached. If the saturation is reached, the particles 10 are permanently magnetized. An external magnetic field 24 is no longer necessary thereafter.

The intensity of the necessary magnetic field 24 as well as the necessary size, number and material of the magnetic particles 10 to be added depend on the size and shape of the sorbing particles of granular material 5 as well as the occurring or expected external effects such as shock, vibration or temperature.

The intensity of the necessary magnetic field 24 depends on the magnetic properties of the magnetic particles 10. Such an intensity is obtained, for example, from a hysteresis curve of the material used, as is shown, e.g., in FIG. 4.

The product of flux density B and field intensity H with the abbreviation $B \times H_{max}$ represents the technically usable magnetic power in the application. $B \times H_{max}$ is the magnetic energy related to the volume of the magnet.

Figure 4:
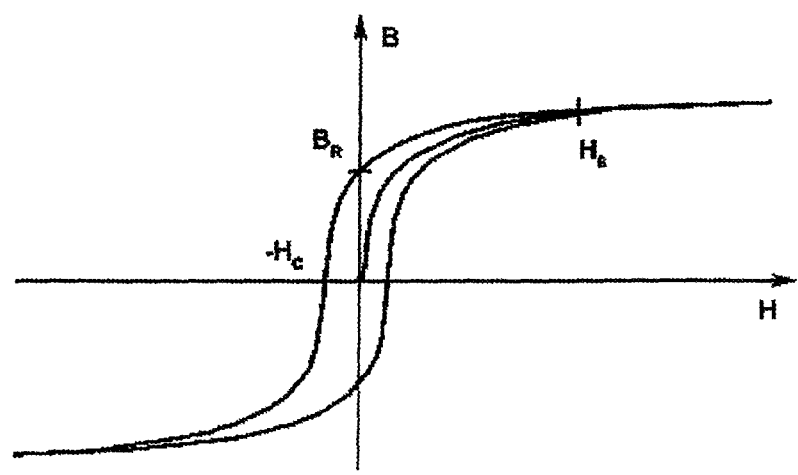
FIG. 4 is a schematic view of a hysteresis curve.

The coercitive field strength $H_C$ and the remanence $B_R$ are shown in the hysteresis curve shown in FIG. 4. The coercitive field strength $H_C$ is the field intensity that must be applied to fully demagnetize the magnet (flux density B=0) and is defined as the intersection of the hysteresis curve with the field intensity axis H. The higher the coercitive field strength, the greater is the resistance of the magnet to demagnetization by external fields. The flux density that occurs without external field is called remanence $B_R$. It is read at the intersection of the hysteresis curve with the flux density B axis.

A concrete exemplary embodiment for producing a sorbing granular material 20 according to the present invention will be explained below. For example, 1,075 g of $CO_2$ absorbent are mixed with 425 g of steel shot of a size of 0.2 mm to 0.4 mm in the particles of granular material 5. This mixture is granulated into half-beads with a diameter of approx. 2 mm to 4 mm and dried to an $H_2O$ content of 14% to 23%. The absorbent used is supplied by the applicant under the trade name "Drägersorb 400" and comprises calcium hydroxide, alkali hydroxide and water.

The absorbent used may be used as a high-performance breathing lime for the absorption of carbon dioxide in closed-circuit respirators.

The steel shot component present accounts for 28.3 wt. %. A comparison of the $CO_2$ absorption capacity showed a 35% reduction compared to untreated "Drägersorb 400."

The absorbing granular material 20 thus obtained was filled into a filter housing and compacted with a magnetic field 24 generated by four neodymium permanent magnets 26, holding force per magnet 20 kg.

The absorbing granular material 20 according to the present invention, made available on the basis of Drägersorb breathing lime, can be used in an anesthesia apparatus for receiving expired breathing air of a patient.

A breathing lime based on this absorbing granular material 20 may be used, in general, in an anesthesia apparatus, in a closed-circuit respirator or a regeneration type respirator or form a filter for an anesthesia apparatus. Since the magnetic sorbing particles of granular material 5 form a stable granular material composite, a relative motion of the particles of granular material 5 among each other is no longer possible, so that a possible cause of the duct formation mentioned in the introduction is eliminated. Furthermore, abrasion dust of the absorbent/adsorbent as another undesired effect of the relative motion is reduced or eliminated altogether, so that health hazard to the user, which is due to the abrasion dust in the airways of the user, can be reduced.

In order not to reduce the absorption capacity too greatly, it is necessary to possibly use substances that have a high magnetic flux density or, in case of soft magnetic or ferromagnetic materials, reach their magnetic saturation already at very low magnetic field intensities of the exciting magnetic field 24.

The steel shot used as a magnetic particle 10 is a ferromagnetic material that directs its magnetic moment in parallel to the magnetic field acting from the outside and even boosts it.

The relative permeability $\mu_r$ as a characteristic for classifying magnetic materials is between 300 and 10,000. Amorphous metals with relative permeabilities $\mu_r$ between 700 and 500,000 and nanocrystalline metals with relative permeabilities $\mu_r$ between 20,000 and 150,000 are conceivable as well.

Another feature of the solution being proposed is that the magnetic fields are always magnetic fields that are constant in the pole direction.

In addition, the magnetic particles 10 are distributed randomly concerning the direction of their magnetic action in the absorber granular material 20 in order to make possible an unordered arrangement of the granular material 20 among each other.

In a process for producing the sorbing granular material 20, the desired sorbing raw material, which is usually in the form of an aqueous substance, is provided at first. The raw material is then mixed with the magnetizable particles 10. A plurality of particles of granular material 5 are then formed from the sorbing raw material.

To do so, the raw material mixed with the magnetizable particles 10 is filled into corresponding molds and then pressed and dried. However, it is also conceivable that the raw material is mixed with the magnetizable particles 10 only after filling into suitable molds, so that these are arranged on the outer surfaces 15 of the particles of granular material 5. In addition or instead of this procedure, magnetizable particles 10 may also be brought into the bottoms of the molds in the desired number prior to filling.

The particles of granular material 5 may also be produced by punching by the raw material being placed on a suitable substrate and subsequently processed into particles of granular material 5 of the desired size with a punching tool.

The use of the sorbing granular material 20 is suitable for both cylindrical and cuboid filter cartridge geometries or geometries of breathing lime and/or shipping containers. The sorbing granular material is filled into a filter insert or in an absorption, shipping or storage vessel to form a filling. The particles of granular material 5 form a compacted sorbing granular material 20 by means of magnetic attracting forces between the magnetizable particles 10 by application of a magnetic field via an electro magnet or a permanent magnet 26. The magnetic field may be applied for compaction before use or in the vicinity of use (and the compaction may be reversed).

Figure 5:
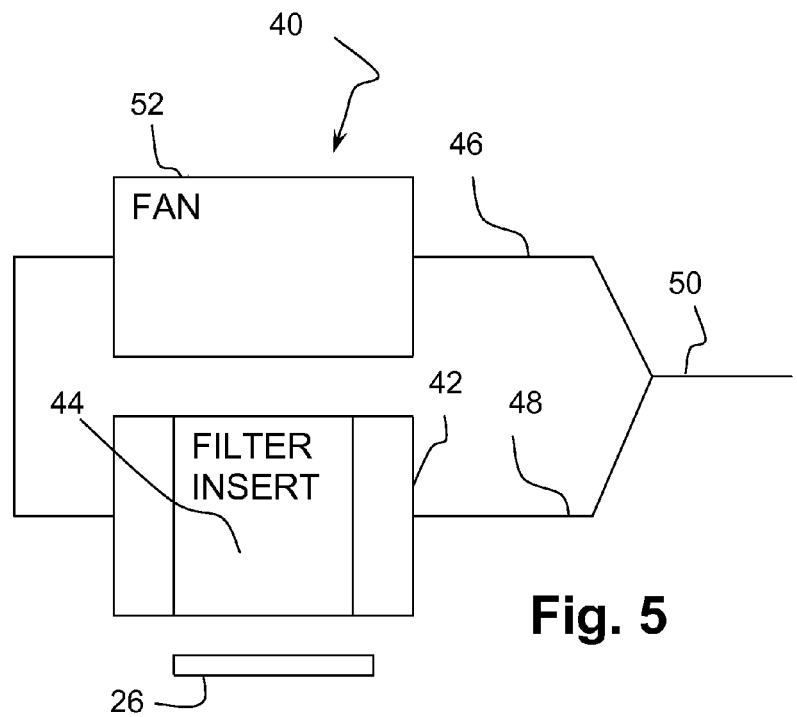
FIG. 5 is a schematic view of a respirator according to the invention.
Figure 6:
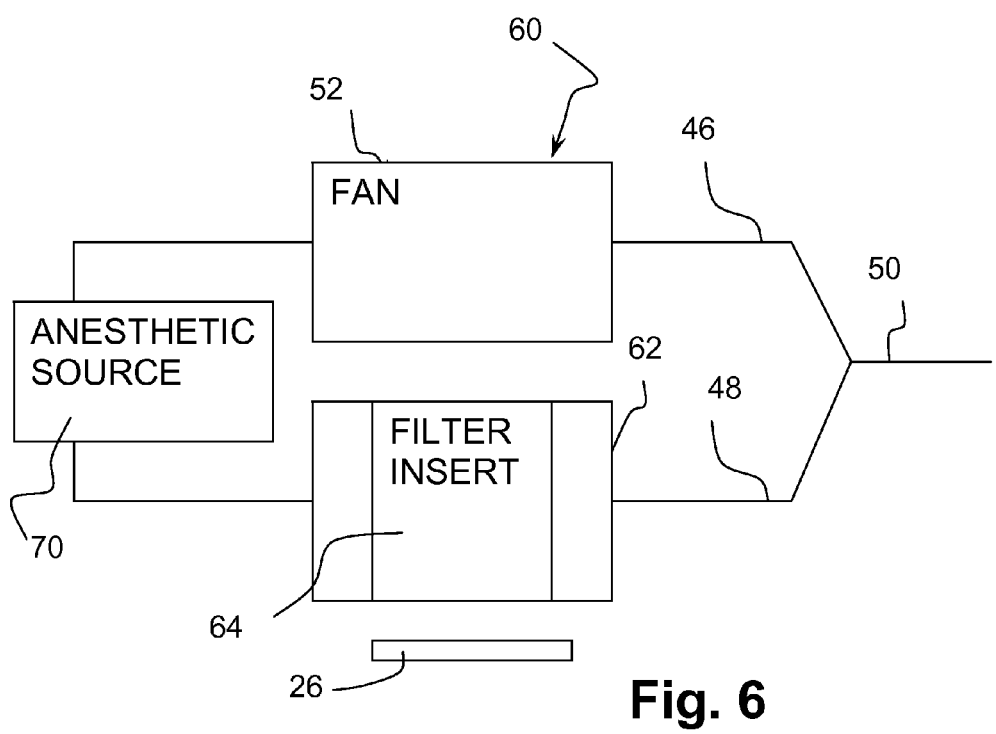
FIG. 6 is a schematic view of an anesthesia apparatus according to the invention.

Such a filter cartridge 44, 64 is provided filled with sorbing granular material 20 for use in a respirator (also known as ventilator) 40 as shown in FIG. 5 or in an Anesthesia apparatus 60 as shown in FIG. 6.

The respirator 40 includes a respirator filter 42 with the filter insert 44 comprising a container and a filling within the container. The filling comprises the sorbing granular material 20. The respirator 40 may also include respirator features such as an inspiration line 46 connected to the respiration filter 42, an expiration line 48 connected to the respiration filter 42, a patient connection 50 connected to the inspiration line 46 and the expiration line 48 and a fan (or pressurized gas source) 52. The filter insert 44 is removably inserted into the respirator filter 41 for absorbing components of expired breathing air. The respirator 40 may be provided with an electro magnet or a permanent magnet 26 to change or reverse the compaction of the sorbing granular material 20.

The anesthesia apparatus 60 includes an anesthesia apparatus filter 62 with the filter insert 64 comprising a container and a filling within the container. The filling comprises the sorbing granular material 20. The anesthesia apparatus 60 may also include anesthesia apparatus features such as an inspiration line 46 connected to the anesthesia apparatus filter 62, an expiration line 48 connected to the anesthesia apparatus filter 62, a patient connection 50 connected to the inspiration line 46 and the expiration line 48 and a fan (or pressurized gas source) 52. An anesthetic source 70 is connected to the inspiration line 46 and to the expiration line 48. The filter insert 64 is removably inserted into the anesthesia apparatus filter 62 for absorbing components of expired breathing air. The anesthesia apparatus 60 may be provided with an electro magnet or a permanent magnet 26 to change or reverse the compaction of the sorbing granular material 20.

While specific embodiments of the invention have been shown and described in detail to illustrate the application of the principles of the invention, it will be understood that the invention may be embodied otherwise without departing from such principles.

APPENDIX

LIST OF REFERENCE NUMBERS

5 Particle of granular material
10 Magnetizable particles
15 Outer surface
220 Granular material
22 Boundary
24 Magnetic field
26 Magnet
40 Respirator
42 Respirator filter
44 Filter insert
46 Inspiration line
48 Expiration line
50 Patient connection
52 Fan (or pressurized gas source)
60 Anesthesia apparatus
62 Anesthesia apparatus filter
64 Filter insert
70 Anesthetic Source

What is claimed is:

1. A sorbing granular material for a respirator, the sorbing granular material comprising:
   a sorbing raw material mass; and
   magnetizable particles, wherein the sorbing mass is mixed at least partly with said magnetizable particles and the sorbing raw material is granualized by shaping or punching the sorbing raw material to form a plurality of particles of granular material of a defined size, each including material of the sorbing mass and some of the magnetizable particles, are formed and upon magnetization of said magnetizable particles, said particles of granular material form a compacted sorbing granular material form with a compaction being based on magnetic attracting forces between said magnetizable particles, wherein said compaction is reversible and a relative movement of the particles of granular material is limited by attractive forces between the magnetizable particles wherein the absorbing granular material comprises breathing lime for absorbing components of expired breathing air, whereby gas flows through the compacted sorbing granular material form in an anesthesia apparatus or a closed-circuit respirator or a regeneration type respirator and during gas flow through the compacted sorbing granular material form, magnetic attracting forces act between the magnetized particles of the particles of granular material to limit a relative movement of the particles of granular material and to prevent or reduce a motion between the particles of granular material and a granular material container wall.

2. A sorbing granular material in accordance with claim 1, wherein said magnetizable particles are arranged on outer surfaces of said particles of granular material.

3. A sorbing granular material in accordance with claim 1, wherein:
   the sorbing granular material possesses absorbing and/or adsorbing properties; and
   the particles of granular material have a diameter of from 2 mm to 4 mm.

4. A sorbing granular material in accordance with claim 1, wherein said magnetizable particles comprise at least one of soft magnetic particles and hard magnetic particles and are added to said particles of granular material.

5. A sorbing granular material in accordance with claim 4, wherein said soft magnetic particles comprise at least one of: metal particles with a relative permeability between 300 and 10,000; amorphous metal particles with a relative permeability between 700 and 500,000; and nanocrystalline metal particles with a relative permeability between 20,000 and 150,000.

6. A sorbing granular material in accordance with claim 4, wherein said soft magnetic particles are produced from at least one of: iron oxide; iron powder; and steel.

7. A sorbing granular material in accordance with claim 4, wherein said hard magnetic particles are produced from at least one of: hard ferrite; aluminum-nickel-cobalt: neodymium-iron-boron; and samarium-cobalt.

8. A sorbing granular material in accordance with claim 1, wherein:
   said magnetizable particles are magnetized; and
   the magnetization of the magnetizable particles occurs by subjecting the magnetizable particles to magnetic forces of an electromagnet or of a permanent magnet.

9. A sorbing granular material in accordance with claim 1, wherein the absorbing granular material is a part of an absorber cartridge of an anesthesia apparatus, a closed-circuit respirator or a regeneration type respirator.

10. A device comprising:
    a filter insert comprising a container and a filling within the container, the filling comprising a sorbing granular material comprising:
    a sorbing raw material mass; and
    magnetizable particles, wherein the sorbing raw material mass is mixed at least partly with said magnetizable particles and granualized by shaping or punching the sorbing raw material to form particles of granular material, each including material of the sorbing mass and some of the magnetizable particles, and upon magnetization of said magnetizable particles, said particles of granular material form a compacted sorbing granular material form with a compaction being based on magnetic attracting forces between said magnetizable particles, wherein said compaction is reversible and a relative movement of the particles of granular material is limited by attractive forces between the magnetizable particles, whereby breathing gas flows through the compacted sorbing granular material, in an anesthesia apparatus or a closed-circuit respirator or a regeneration type respirator, and during gas flow through the compacted sorbing granular material, magnetic attracting forces act between magnetized particles of the granular material to limit a relative movement of the magnetized particles of the granular material and prevent or reduce a motion between particles of the granular material and between the particles of the granular material and a granular material container wall.

11. A device according to claim 10, further comprising:
    a respirator filter;
    an inspiration line connected to said respiration filter and an expiration line connected to said respiration filter; and
    a patient connection connected to said inspiration line and said expiration line wherein said filter insert is a respiration filter insert and is inserted in said respirator filter with expired breathing gas passing through the compacted sorbing granular material filling for absorbing components of the expired breathing gas.

12. A device according to claim 10, further comprising:
    an anesthesia apparatus filter;
    an inspiration line connected to said anesthesia apparatus filter and an expiration line connected to said anesthesia apparatus filter;
    an anesthetic source connected to said inspiration line and said expiration line; and
    a patient connection connected to said inspiration line and said expiration line wherein said filter insert is an anesthesia apparatus filter insert and is inserted in said anesthesia apparatus filter with expired breathing gas passing through the compacted sorbing granular material filling for absorbing components of expired breathing air gas.

13. A device according to claim 10, further comprising:
    a respirator filter;
    an inspiration line connected to said respiration filter and an expiration line connected to said respiration filter, wherein:
    the filter insert is a respiration filter insert and is inserted in said respirator filter with expired breathing gas passing through the compacted sorbing granular material filling for absorbing components of expired breathing gas;
    the respirator filter, the inspiration line and the expiration line are a part of a closed-circuit respirator; and
    the absorbing granular material comprises one of breathing lime and activated carbon.

14. A device according to claim 10, wherein:
the absorbing granular material comprises breathing lime for absorbing components of expired breathing air for an anesthesia apparatus, a closed-circuit respirator or a regeneration type respirator
the magnetizable particles are arranged on outer surfaces of said particles of granular material; and
the particles of granular material have a diameter of from 2 mm to 4 mm.

15. A device according to claim 10, wherein:
the absorbing granular material comprises active carbon for absorbing components of expired breathing air for an anesthesia apparatus, a closed-circuit respirator or a regeneration type respirator
the magnetizable particles are arranged on outer surfaces of said particles of granular material; and
the particles of granular material have a diameter of from 2 mm to 4 mm.

16. A device comprising:
a filter/absorber insert comprising:
a container comprising a container wall with a breathing gas inlet and a breathing gas outlet;
a compacted sorbing granular material filling comprised of magnetized particles of granular material with magnetic attracting forces acting between the magnetized particles of granular material to define a compacted state of the compacted sorbing granular material within the container wall of the container, wherein the compaction is reversible, the particles of granular material comprising:
a sorbing material; and
magnetizable particles, wherein the sorbing material is mixed at least partly with the magnetizable particles and is granualized to form the particles of granular material particles having a diameter of from about 2 mm to 4 mm, with the compacted sorbing granular material filling having a form corresponding to the container wall of the container and a compaction of magnetized particles of granular material based on magnetic attracting forces between the magnetized particles of granular material, wherein the compaction is reversible and a relative movement of the magnetized particles of granular material is limited and a motion between the granular material and the container wall is prevented or greatly reduced by attractive forces between the magnetized particles of granular material, whereby breathing gas flows through the granular material filling form in an anesthesia apparatus or a closed-circuit respirator or a regeneration type respirator and during gas flow through the granular material filling form, magnetic attracting forces act between the magnetized particles of granular material to limit a relative movement of the magnetized particles of granular material and to prevent of reduce a motion between the granular material and a granular material container wall as the breathing gas flows through the granular material filling form.

17. A device according to claim 16, further comprising:
a respirator filter;
an inspiration line connected to the respiration filter and an expiration line connected to the respiration filter; and
a patient connection connected to the inspiration line and the expiration line wherein the filter insert is a respiration filter insert and is inserted in the respirator filter with expired breathing gas passing through the compacted sorbing granular material filling for absorbing components of the expired breathing gas, wherein the sorbing material comprises one of breathing lime and activated carbon.

18. A device according to claim 16, further comprising:
an anesthesia apparatus filter;
an inspiration line connected to the anesthesia apparatus filter and an expiration line connected to the anesthesia apparatus filter;
an anesthetic source connected to the inspiration line and the expiration line; and
a patient connection connected to the inspiration line and the expiration line wherein the filter insert is an anesthesia apparatus filter insert and is inserted in the anesthesia apparatus filter with expired breathing gas passing through the compacted sorbing granular material filling for absorbing components of the expired breathing gas, wherein the sorbing material comprises one of breathing lime and activated carbon.

19. A device according to claim 16, further comprising:
a respirator filter;
an inspiration line connected to the respiration filter and an expiration line connected to the respiration filter, wherein:
the filter insert is a respiration filter insert and is inserted in the respirator filter with expired breathing gas passing through the compacted sorbing granular material filling for absorbing components of the expired breathing gas; and
the respirator filter, the inspiration line and the expiration line are a part of a closed-circuit respirator, wherein the sorbing material comprises one of breathing lime and activated carbon.

20. A device according to claim 16,
further comprising:
a magnet positioned adjacent to the filter insert to reverse a state of compaction or change a state of compaction;
said magnetizable particles are magnetized; and
the magnetization of the magnetizable particles occurs by subjecting the magnetizable particles to magnetic forces of an electromagnet or of a permanent magnet.

* * * * *